United States Patent [19]

Allen et al.

[11] 4,141,345
[45] Feb. 27, 1979

[54] CERVICAL DILATION MEASUREMENT INSTRUMENTS

[75] Inventors: David W. Allen, Thornbury; John A. Richardson, Easter Compton; Ian A. Sutherland, Harpenden, all of England

[73] Assignee: National Research Development Corporation, London, England

[21] Appl. No.: 756,836

[22] Filed: Jan. 5, 1977

[30] Foreign Application Priority Data

Jan. 8, 1976 [GB] United Kingdom ............... 00650/76

[51] Int. Cl.² ............................................. A61B 5/10
[52] U.S. Cl. .................................. 128/2 S; 33/149 J; 33/174 D; 128/361
[58] Field of Search .............. 128/2 S, 361; 33/143 L, 33/148 H, 149 J, 174 D

[56] References Cited

U.S. PATENT DOCUMENTS

| | | | |
|---|---|---|---|
| 2,924,220 | 2/1960 | Von Micsky | 128/361 |
| 3,273,559 | 9/1966 | Evans | 128/361 |
| 3,420,222 | 1/1969 | Noe et al. | 128/2 S |
| 3,937,212 | 2/1976 | Fletcher | 128/2 S |

*Primary Examiner*—Kyle L. Howell
*Attorney, Agent, or Firm*—Finnegan, Henderson, Farabow & Garrett

[57] ABSTRACT

Cervical dilation is measured by a V-shaped caliper instrument having connectors on the free ends of the caliper arms for securement to respectively opposed portions of the cervix, and a transducer coupled with the arms to provide an electric signal representing their mutually relative positions. The transducer suitably comprises strain gages mounted on a spring acting between the arms. The connectors can be toothed spring clips pivoted on the arms, but are preferably pins projecting generally parallel to the arms from the underfaces of outwardly turned free end portions thereof. In the latter case the arms preferably have spring guard strips extending alongside their outer faces at their ends.

11 Claims, 5 Drawing Figures

CERVICAL DILATION MEASUREMENT INSTRUMENTS

This invention concerns medical instruments and more particularly such instruments for measuring cervical dimensions to assess the progress of labor.

While highly sophisticated techniques have been developed for accelerating labor and monitoring the fetus, it is still common practice for the obstetrician to resort to regular vaginal examination in order to estimate cervical dilatation and thereby assess the progress of labor. However, these examinations are uncomfortable to the patient, risk introducing infection into the uterus, and are inaccurate, these disadvantages being amplified if serial examinations are carried out by different observers.

There have been sporadic proposals for instruments to monitor cervical dilatation, but these have been employed primarily for purposes of research and have failed to gain general application in routine practice, mainly because the instruments were bulky and uncomfortable to the patient. Examples of such proposals are that of Friedmann E. A. (1956) Amer. J. Obstet. Gynae., 71, 1189 and that of Embry M. P. and Seiner H. (1965) J. Obstet. Gynae, 75, 225. Clearly there is a need for an improved instrument which can be used in routine practice to monitor cervical dilatation and thereby ease labor management.

An object of the present invention is to meet this need and there is accordingly provided a medical instrument comprising a pair of similar arms pivotally connected together at one pair of respective ends to form a generally V-shaped caliper assembly for location in the vagina, a pair of connectors respectively mounted on the other ends of said arms for securement to opposed portions of the cervix, and an electropositional transducer coupled with said arms to provide a signal representing the relative positions of said arms and thereby cervical dilatations.

Preferably a spring is connected between the arms of the instrument to bias the arms to move in mutually opposite directions to open or close the caliper assembly. In this case it is also preferred that the transducer comprise at least one strain gages mounted on the spring, such gage having an electrical characteristic which varies with the stressed condition of the spring.

In order that the invention may be fully and clearly understood, the same will now be described, by way of example, with reference to the accompanying drawings, in which:

FIG. 1 schematically illustrates an initial embodiment of the invention in use;

Figure 4:
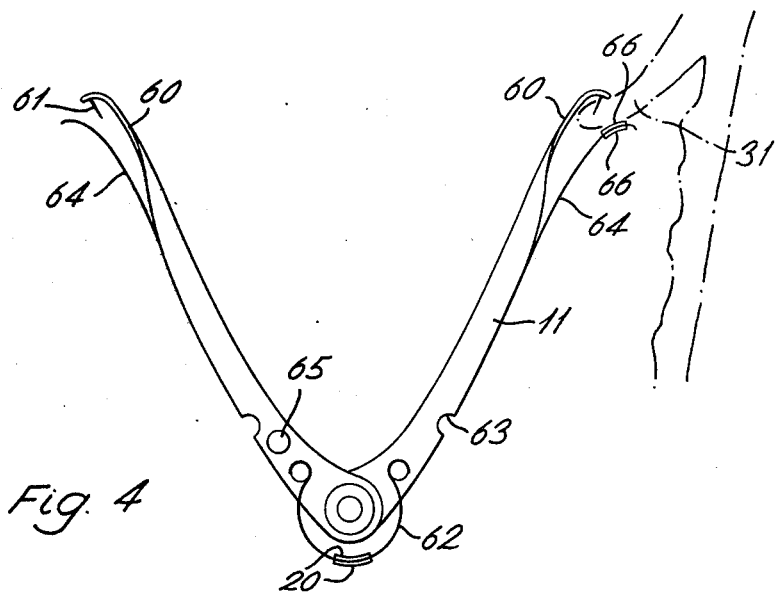

FIG. 4 schematically illustrates a later embodiment of the invention, and

Figure 5:
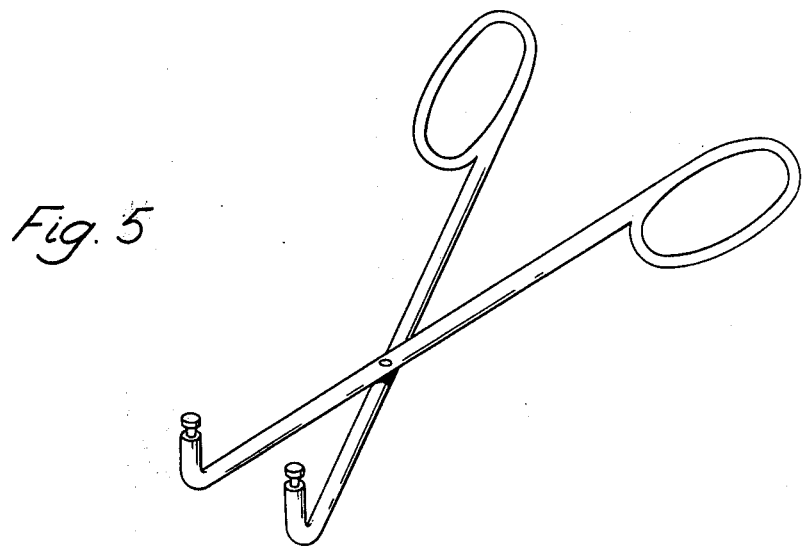

FIG. 5 similarly illustrates an applicator for this later embodiment.

Figure 1:
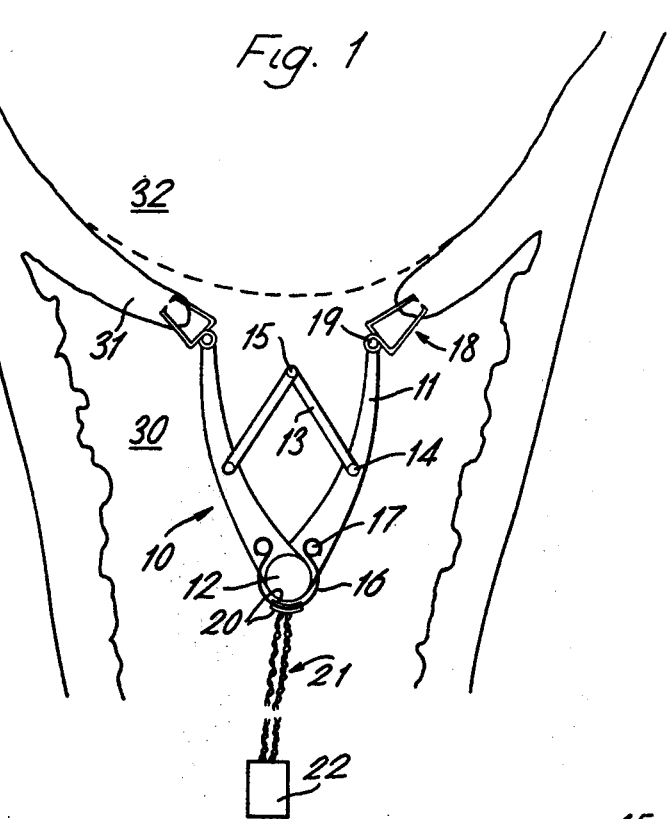

The instrument of FIG. 1 is denoted at 10 and comprises two like curved arms 11 which are pivotally connected together at 12 at one pair of corresponding ends to form a generally V-shaped caliper assembly. This assembly also includes two like linkage members 13 respectively pivotally connected at 14 at one end to an intermediate portion along one of the arms, and pivotally connected together at 15 at their other ends.

In addition the caliper assembly is provided with a C-shaped leaf spring 16 respectively pivotally connected at 17 at its ends to the arms adjacent the pivot 12, with the main body of the spring embracing the axis of rotation of this pivot, and with the spring acting to bias the arms together in a closing movement for the caliper assembly.

The instrument also comprises a pair of like sprung clips 18 respectively pivotally connected at 19 to the free ends of the arms, and an electropositional transducer coupled with the arms. This transducer includes two like variable-resistance strain gages 20 of printed circuit form respectively bonded on the inner and outer faces of the spring 16. These gages are connected in adjacent arms of a bridge circuit by leads 21, reference resistors of this circuit being incorporated in a connector 22 at the free ends of the leads.

FIG. 1 shows the instrument 10 located in use, with the whole of the caliper assembly introduced into the vagina 30 and the clips 18 respectively secured to substantially diametrally opposed portions of the cervix 31 with the assembly extending therefrom into the vagina relative to the uterus 32. In this location, dilatation of the cervix during the progress of labor causes the caliper assembly to open correspondingly against the bias of the spring 16, and variation of this opening movement is represented by variation in the output signal of the bridge circuit in which the transducer strain gages 20 are connected. More specifically, as the caliper assembly opens so also does the spring to apply respective tensile and compressive strains to the gages on the inner and outer surfaces of the spring. These strains vary the resistances of the gages in differential manner and so corresponding variation in the bridge circuit output is enhanced compared to that which would be obtained with use of a single gage. This use of two gages is additionally advantageous in reducing errors which may otherwise arise from temperature variations, this reduction resulting from the fact that such variations affect the gages similarly in the bridge circuit.

The illustrated instrument is advantageous in other respects in that, apart from the emergence of the leads 21, it is wholly located in the vagina without the projection therefrom of rigid members which can cause discomfort. The instrument need not be handled other than during introduction and withdrawal, the instrument being rendered sterilisable by encapsulating the strain gages and lead connections thereto with a suitable material, so that any risk of infection is minimised.

During development of the instrument of FIG. 1, various forms of conventional clips were found to disengage from the cervix. This is thought to arise from the fact that the cervix comprises soft tissue which tends to move in an evasive manner when clipping is attempted, and the fact that dilatation involves both radial and circumferential movement of the cervix which can also lead to disengagement. Those conventional clips which have no barbs are found to disengage readily and this is probably caused by both of the above factors, and those with barbs commonly have too many too widely distributed such that the second factor can cause disengagement by tearing of the cervical tissue.

Figure 2:
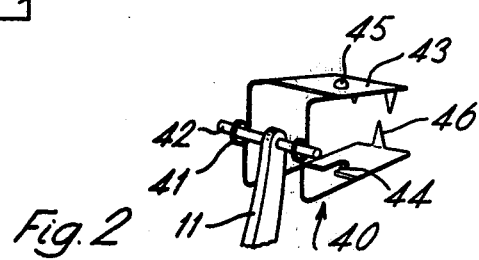
FIG. 2 illustrates a clip of this embodiment in more detail.

In any event the clip of FIG. 2 was produced to reduce the difficulties encountered with conventional clips. The illustrated clip comprises two lengths of spring wire 40 formed to like U-shapes of which the bases are coiled at 41 around the respective end portions of a pivot pin 42 fixed transversely through the end of the relevant arm 11. Each coil 41 forms a spring acting to close together the associated U-arm portions of the wire. Two plates 43 are respectively fixed to span the gaps between corresponding pairs of the U-arm portions. The one of these plates which is nearer to the pivot 12 when the clip projects laterally outwardly from the caliper assembly as shown in FIG. 1 is formed with a slot 44 opening into the edge of the plate nearer to the pivot pin 42, and the other plate is formed with a notch 45 facing the slot 44. The plates are formed with barbs 46 adjacent their outer free edges, which barbs closely intermesh within a very small zone of the plates as the latter close together. Alternatively a single barb and interengaging hole may be provided on the respective plates.

Figure 3:
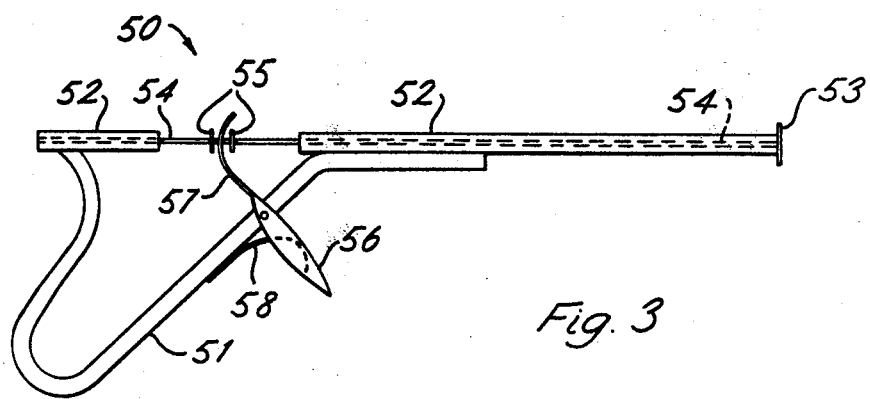
FIG. 3 illustrates an applicator for this clip.

The illustrated clip is used with the applicator 50 of FIG. 3 which was developed for this purpose. This applicator comprises a pistol grip 51 formed from suitably shaped metal tube, and two further lengths of such tube are secured in coaxial alignment along the rear and forward portions of the pistol grip to form a two-part barrel 52. The forward end of the barrel is provided with an outward radial flange 53. A rod 54 is located in the barrel and is provided with two closely spaced radial flanges 55 on the portion of the rod passing between the two parts of the barrel. The pistol grip also carries a trigger 56 pivotally mounted thereon, this trigger having an upward extension 57 which is forked to engage the rod 54 between the flanges 55. Also, a spring 58 acts between the trigger and the pistol grip to bias the trigger to a position in which the forward end of the rod is just withdrawn into the barrel. In use of this applicator with the clip of FIG. 2 the forward end of the barrel is located in the slot 44; the trigger is depressed to project the rod from the barrel to engage the rod in the notch 45 and the barrel flange against the slotted plate, thereby to open the clip and at the same time hold the same for positioning relative to the cervix; and finally the trigger is released to allow the clip to close when the clip has been positioned as required.

However, while the instrument, clip and applicator of FIGS. 1 to 3 can be used successfully, trials indicate that such success requires a length of experience which may act against ready acceptance for routine clinical utilisation. Accordingly the invention has been developed further to facilitate its practical application.

FIG. 4 illustrates one embodiment of an instrument which has resulted from this further development. This instrument is similar in some respects to that of FIG. 1 and it is convenient to discuss the former in terms of its differences from the latter while employing the same reference numerals for common components.

A first difference is omission of the clips 40 which, notwithstanding their securement capability, require skill and practice in use. In place of each clip 40, the relevant arm is narrowed to a strip form over its free end portion 60, and this portion is turned outwardly adjacent its end through approximately a right angle and provided with a pin 61 which projects from its underface approximately parallel with the portion 60 leading to the turn therein. In addition, the spring 16 is changed to a similar spring 62 which acts to bias the arms outwardly in an opening movement for the caliper assembly.

The instrument is initially located as before in a closed configuration, but in this case the portions 60 of the arms are passed through the cervical canal, or under the rim of a partially dilated cervix, and are then withdrawn after a partial opening movement so that, in the result, the portions 60 seat around the rim and the pins 61 penetrate the inner surface thereof. Removal of the instrument involves a reverse of this procedure.

These procedures are facilitated by the provision of two notches 63 respectively located in the lateral outer surfaces of the arms 11, which notches co-operate with the applicator of FIG. 5. This applicator has the general form of scissor-acting forceps, but has the free end portions of its arms turned perpendicularly to the plane of the scissor action and circumferentially notched or grooved to seat in the notches 63 of the instrument. Thus the applicator can be used to hold the instrument and effect controlled opening and closure thereof.

It will also be seen that two additional components are provided in respective association with each portion 60 of the instrument. Each such component is in the form of a strip 64 of spring material which is secured to the laterally outer surface of the associated arm 11 partway therealong and extends alongside the portion 60 in a similar shape thereto but in a divergent manner. These components abut the outer surface of the cervix when the instrument is located, and close over the pins 61 if tissue is engaged during retraction thereby to guard against damage to the vagina.

Another difference in this instrument is that the linkage members 13 are omitted. The reason for this omission is that the linkage members were found on occasion to be engaged by the descending fetal head and the instrument dislodged.

Further differences are also present in the instrument of FIG. 4 to indicate current and continuing development.

One such difference is the omission of the leads 21 and connector 22 for direct connection of the instrument with extracorporeal monitoring equipment, and substitution of a transmitter 65 of integrated circuit form to serve as part of a telemetry system which communicates data to the monitoring equipment. Moreover, this telemetry system can be of multi-channel form to communicate data concerning other parameters of interest, and the instrument can serve as a support for transducers to measure such parameters as intrauterine pressure and fetal heart rate.

Another parameter of possible interest, but for which no instrument suited to routine clinical use appears to be available, is that of cervical effacement. The instrument of FIG. 4 can be modified to take account of this by the provision of strain gages 66 on one of the guard spring strips, such gauges acting, in similar manner to gages 20, to indicate any change in position of strip 64 relative to its rest position adjacent the associated arm portion 60 and therefore the thickness of the cervix therebetween.

While the invention has been described with more particular reference to the accompanying drawings, it will be apparent that these drawings represent evolving prototypes in a continuing development and that further modification can be made without departing from the scope of the invention as defined in the appendant claims.

We claim:

1. A medical instrument comprising a pair of similar arms connected together adjacent one pair of respective ends to form a generally V-shaped caliper assembly for location in the vagina, a pair of connectors respectively mounted adjacent the other ends of said arms for securement to opposed portions of the cervix, a spring connected between said arms and acting to bias said arms for movement in mutually opposite directions, and an electropositional transducer coupled with said arms to provide a signal representing the relative positions of said arms and thereby cervical dilatation, said transducer including at least one strain gage mounted on said spring and having an electrical characteristic which varies with the stressed condition of said spring.

2. An instrument according to claim 1 wherein said spring is of bowed strip form extending between said arms, said spring having two of said gages respectively mounted on the opposite faces of said strip form to provide a differential electrical signal representing said stressed condition.

3. An instrument according to claim 1 wherein said connectors each comprise a toothed, spring clip pivotally connected to the relevant one of said arms.

4. An instrument according to claim 1 wherein each of said arms is turned laterally outwardly adjacent said other end, and said connectors comprise pins projecting from the undersurfaces of such turned end portions.

5. An instrument according to claim 4 comprising a pair of guard members of strip spring form respectively connected to each of said arms, said members extending similarly adjacent, and in spaced relation, to said turned in portions to face toward said pins.

6. An instrument according to claim 1 comprising at least one further transducer mounted thereon to provide a further electrical signal representing a further body function parameter.

7. An instrument according to claim 5 comprising a further transducer including at least one further strain gage mounted on one of said guard members, each such further gauge having an electrical characteristic which varies with the stressed condition of said one member, said further transducer providing an electrical signal representing cervical effacement.

8. An instrument according to claim 1 forming part of a telemetry system including extracorporeal receiving equipment, said instrument including a transmitter carried by said assembly and connected for transmitting said signal to the extracorporeal receiving equipment of the telemetry system.

9. A medical instrument comprising a pair of similar arms connected together at one pair of respective ends to form a generally V-shaped caliper assembly for location in the vagina, said arms each turning at its free end portion laterally outwardly relative to said assembly for connection of the free end portions of the cervix, respective pins connected to each of said arms and projecting from the undersurfaces of said turned free end portions, a pair of guard members of strip spring form respectively connected to said arms and extending similarly, adjacent, and in spaced relation, to said turned free end portions for movement towards and away from said pins, and an electropositional transducer coupled with said arms to provide a signal representing the relative positions of said arms and thereby cervical dilatation.

10. A medical instrument comprising a pair of similar arms connected together at one pair of respective ends to form a generally V-shaped caliper assembly for location in the vagina, a pair of connectors respectively mounted on the other ends of said arms for securement to opposed portions of the cervix, a first electropositional transducer coupled with said arms to provide a first electrical signal representing the relative positions of said arms and thereby cervical dilatation, and a second transducer carried by said assembly to provide a second electrical signal representing a further body function parameter.

11. A medical instrument forming part of a telemetry system including extracorporeal receiving equipment comprising a pair of similar arms connected together at one pair of respective ends to form a generally V-shaped caliper assembly for location in the vagina, a pair of connectors respectively mounted on the other ends of said arms for securement to opposed portions of the cervix, an electropositional transducer coupled with said arms to provide a signal representing the relative positions of said arms and thereby cervical dilatation, and a transmitter mounted on said assembly and connected for transmitting said signal to the extracorporeal receiving equipment of the telemetry system.

* * * * *